United States Patent
Weinberg

[19]

[11] Patent Number: 6,042,637
[45] Date of Patent: *Mar. 28, 2000

[54] CORONA DISCHARGE DEVICE FOR DESTRUCTION OF AIRBORNE MICROBES AND CHEMICAL TOXINS

[76] Inventor: Stanley Weinberg, 575 Tigertail Rd., Los Angeles, Calif. 90049

[*] Notice: This patent is subject to a terminal disclaimer.

[21] Appl. No.: 09/161,803

[22] Filed: Sep. 28, 1998

Related U.S. Application Data

[63] Continuation of application No. 08/931,101, Sep. 15, 1997, Pat. No. 5,814,135, which is a continuation-in-part of application No. 08/696,624, Aug. 14, 1996, Pat. No. 5,667,564.

[51] Int. Cl.⁷ ........................................................ B03C 3/32
[52] U.S. Cl. ........................ 96/58; 96/69; 96/80; 96/97; 96/223; 99/451; 361/235; 422/122
[58] Field of Search .................................. 96/26, 55, 59, 96/80, 68, 69, 97, 98, 66, 27, 58, 63, 223, 226, 224, 225; 95/70, 78, 80, 81; 422/4, 22, 121, 120, 122; 323/903; 99/451; 426/237, 240, 248; 361/226, 233, 235; 55/356, 357

[56] References Cited

U.S. PATENT DOCUMENTS

| | | | |
|---|---|---|---|
| Re. 33,927 | 5/1992 | Fuzimura | 96/98 X |
| T868,006 | 11/1969 | Shutack | 55/356 X |
| 2,067,822 | 1/1937 | Biederman | 96/65 X |
| 3,295,440 | 1/1967 | Rarey et al. | 96/97 X |
| 4,163,650 | 8/1979 | Watson et al. | 55/356 X |
| 4,227,894 | 10/1980 | Proynoff | 96/55 |
| 4,244,710 | 1/1981 | Burger | 96/97 X |
| 4,253,852 | 3/1981 | Adams | 96/58 |
| 4,322,786 | 3/1982 | Weber | 361/235 X |
| 4,386,395 | 5/1983 | Francis, Jr. | 363/27 |
| 4,402,716 | 9/1983 | Chiaramonte | 55/356 |
| 4,477,263 | 10/1984 | Shaver et al. | 361/235 X |
| 4,592,763 | 6/1986 | Dietz et al. | 96/80 X |
| 4,670,026 | 6/1987 | Hoenig | 96/97 X |
| 4,689,715 | 8/1987 | Halleck | 361/235 X |
| 4,789,801 | 12/1988 | Lee | 96/26 X |
| 4,811,159 | 3/1989 | Foster, Jr. | 361/231 |
| 4,911,737 | 3/1990 | Yehl et al. | 95/81 |

(List continued on next page.)

FOREIGN PATENT DOCUMENTS

| | | | |
|---|---|---|---|
| 322635 | 7/1989 | European Pat. Off. | |
| 165710 | 8/1991 | Taiwan . | |
| 931625 | 7/1963 | United Kingdom | 96/80 |
| 8201627 | 5/1982 | WIPO . | |

OTHER PUBLICATIONS

Feldman et al, "The Surprising Life of Nitric Oxide", C&EN, pp. 26–38, Dec. 20, 1993.
Wein Products, Inc. Brochure, Los Angeles, California, Undated.
Wein Products, Inc. Brochure, Air Supply VI–350M, Los Angeles, California, Undated.

*Primary Examiner*—Richard L. Chiesa
*Attorney, Agent, or Firm*—Price, Gess & Ubell

[57] ABSTRACT

A miniature air purifier produces a corona discharge surrounding a needle-like emitter point connected to a negative DC power supply. The power supply operates from a nine volt battery and contains a step-up voltage inverter having a single transformer outputting high voltage spikes with a voltage multiplier operating on the output of the inverter. The production of high voltage spikes of about 200 Hz rather than a sinusoidally varying voltage significantly reduces current consumption. The needle-like emitter point is located about ¼-inch from an 80% open mesh metallic grid held at ground potential. Corona discharge at the emitter point ionizes the air and creates ozone, and nitric oxide both of which combine with direct electron impact decomposition to detoxify and destroy a wide variety of airborne pollutants including pathogens, chemicals and allergens. The grid attracts negatively ionized air molecules thereby creating a flow of purified air out of the device and also provides a surface for electroprecipitation of ionized particulates. An alternative embodiment of the present invention can combine a series of emitter points in a sterilizer to provide a microbial neutralization in the food service industry.

24 Claims, 7 Drawing Sheets

U.S. PATENT DOCUMENTS

| | | | |
|---|---|---|---|
| 5,034,032 | 7/1991 | Yikai et al. | 96/97 X |
| 5,055,115 | 10/1991 | Yikai et al. | 96/97 X |
| 5,065,272 | 11/1991 | Owen et al. | 96/97 X |
| 5,159,544 | 10/1992 | Hughey et al. | 323/903 X |
| 5,322,550 | 6/1994 | Park | 96/66 |
| 5,332,425 | 7/1994 | Huang | 96/26 |
| 5,407,469 | 4/1995 | Sun | 361/266 X |
| 5,484,472 | 1/1996 | Weinberg | 96/26 |
| 5,518,531 | 5/1996 | Joannu | 96/55 |
| 5,538,692 | 7/1996 | Joannou | 422/121 |
| 5,656,063 | 8/1997 | Hsu | 95/58 |
| 5,667,564 | 9/1997 | Weinberg | 96/58 |
| 5,814,135 | 9/1998 | Weinberg | 96/58 |

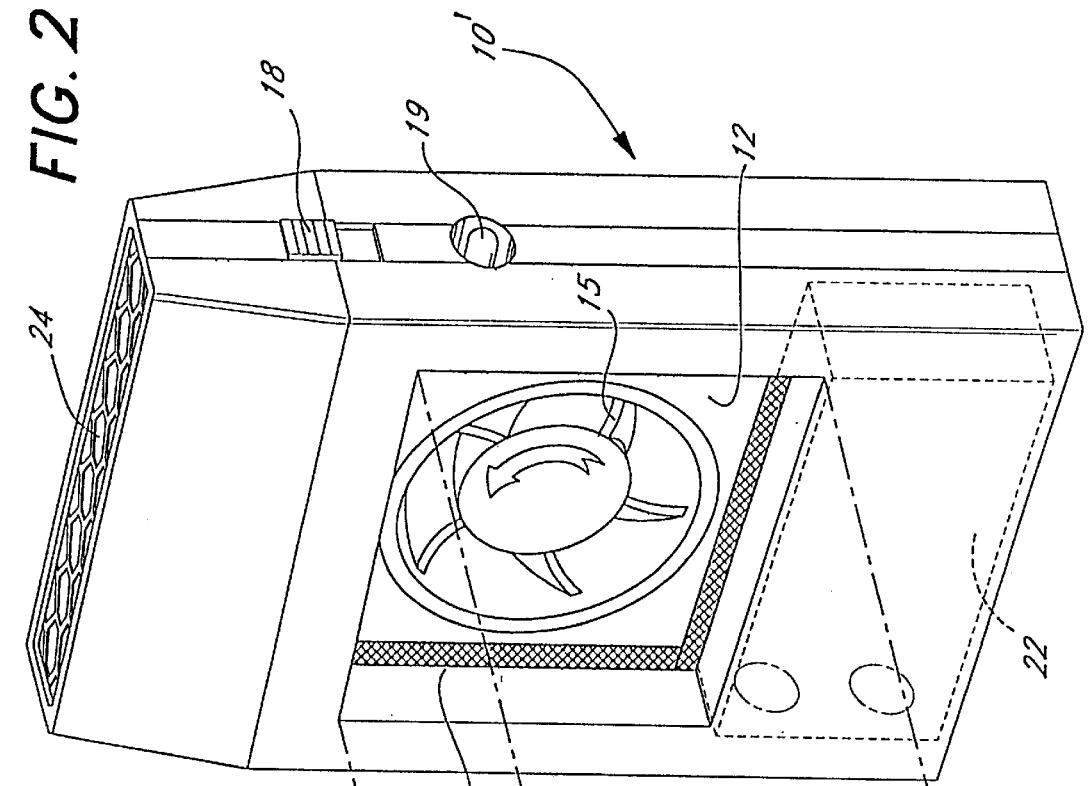
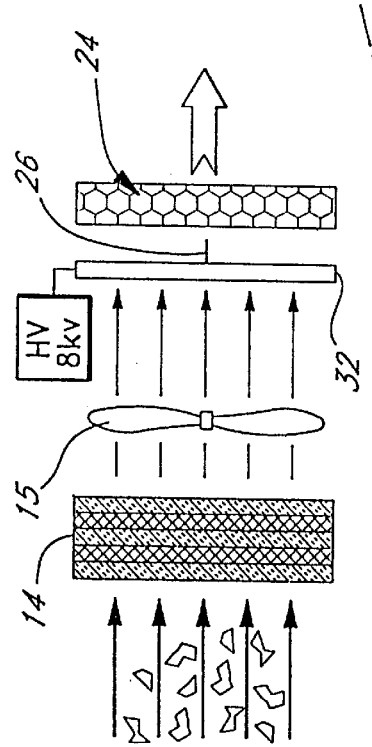

CORONA DISCHARGE DEVICE FOR DESTRUCTION OF AIRBORNE MICROBES AND CHEMICAL TOXINS

RELATED APPLICATIONS

This application is a continuation of Ser. No. 08/931,101, filed on Sep. 15, 1997, now U.S. Pat. No. 5,814,135, which is a continuation-in-part application of Ser. No. 08/696,624, filed on Aug. 14, 1996, now, U.S. Pat. No. 5,667,564.

BACKGROUND OF THE INVENTION

1. Field of the Invention

The present invention involves the field of electronic air purification and, more specifically, a miniature device that generates a corona discharge to detoxify, and circulate air around an individual's face.

2. Description of Related Art

The present invention represents an improvement to the instant inventor's earlier invention entitled "Miniature Air Purifier" filed Feb. 6, 1995, and now issued as U.S. Pat. No. 5,484,472. That patent describes a miniature wearable unit that directs a current of ionized air towards the face of a wearer to help prevent the inhalation of various toxins and irritants that are increasingly present in our environment. For a summary of various earlier approaches to the problems of ameliorating contaminated air, the reader is directed to that earlier patent which is incorporated herein by reference.

The problem of air pollution can hardly be overstated. It has been variously estimated that as many as 80 million Americans suffer from air pollution that results in large numbers of premature deaths each year. It has been reported that children growing up in especially polluted areas like the Los Angeles basin end up with permanently damaged lungs. The problem may be even more acute in large cities of the Third World where environmental controls are more lax than in the United States. While increased governmental regulation poses one solution to the danger, what are affected individuals to do in the meantime? One can install various home air purifying devices, but this does no good when one has to travel about away from the home.

The present inventor has previously offered a portable air purifier as a solution. This earlier miniature air purifier was characterized by its small size allowing it to be worn clipped to one's clothing or on a cord about one's neck. However, the need to incorporate fairly complex electronic circuit board including two inductor components resulted in the unit having a dimension of at least 2½×4×1 inches and weighing at least 7 oz. The circuit of that device required a significant current flow from the battery, which considerably limited battery life. Typically, the unit would operate for about 10–15 hours using a fresh alkaline battery.

The primary routes of air purification in the earlier air purifier were chemical destruction of pollutants by ozone and the corona discharge and electrostatic precipitation of particulates as a result of charging by negative ions. The primary source of air flow was a mass air flow due to acceleration of negatively ionized air molecules towards a grounded metallic grid.

Because ozone can be irritating to the respiratory system, it is desirable to provide a more effective corona discharge for destroying a wider range of chemical pollutants while, at the same time, limiting the amount of ozone emitted. There remains a considerable need for a miniature air purifier that is very efficient at producing a corona discharge for better removal of pollutants and longer battery life with minimal emission of ozone.

OBJECTS AND SUMMARY OF THE INVENTION

It is an object of the present invention to provide a miniature air purifier that can operate for about 50 to 60 hours on a typical nine-volt alkaline battery;

It is a further object of the present invention to provide a miniature air purifier with a simplified circuit using only a single inductive component to reduce the size and weight as well as the cost of the device and to reduce generation of radio frequency interference;

It is a still further object of the present invention to optimize corona discharge purification to maximize killing of pathogens, oxidize the toxins produced by the pathogens, detoxification of chemical pollutants, and neutralization of allergens while minimizing release of ozone; and It is an additional object of the present invention to provide an small wearable air purifier that includes an alternative embodiment that also precleans air by means of pollutant and pathogen filters prior to the corona discharge.

These and additional objects are met by a miniature air purifier that produces a corona discharge around an emitter point connected to a novel 8,000-volt DC power supply. The power supply operates from a single nine-volt battery and contains a step-up voltage inverter having a single transformer and a voltage multiplier operating on the output of the inverter. The needle-like emitter point is located about ¼-inch from an 80% open mesh metallic grid held at ground potential. A corona discharge surrounds the emitter point and produces ionized air as well as destroying pathogens and pollutants with ozone and direct electron impact decomposition. The grid attracts ionized air molecules, thereby creating a mass flow of purified air out of the device, and also provides a surface for electroprecipitation of particulates. An alternative embodiment uses a miniature brushless DC fan to draw room air through a pathogen and pollutant removing filter. The filtered air is exposed to the corona discharge for additional purification and then accelerated out of the device by the emitter point and grid.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 2 shows an alternate embodiment of the device of FIG. 1 with a fan;

FIG. 3 shows a diagrammatic representation of the operation of the device of FIG. 2;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a miniature air purifier with improved efficiency and reduced size.

Figure 1:
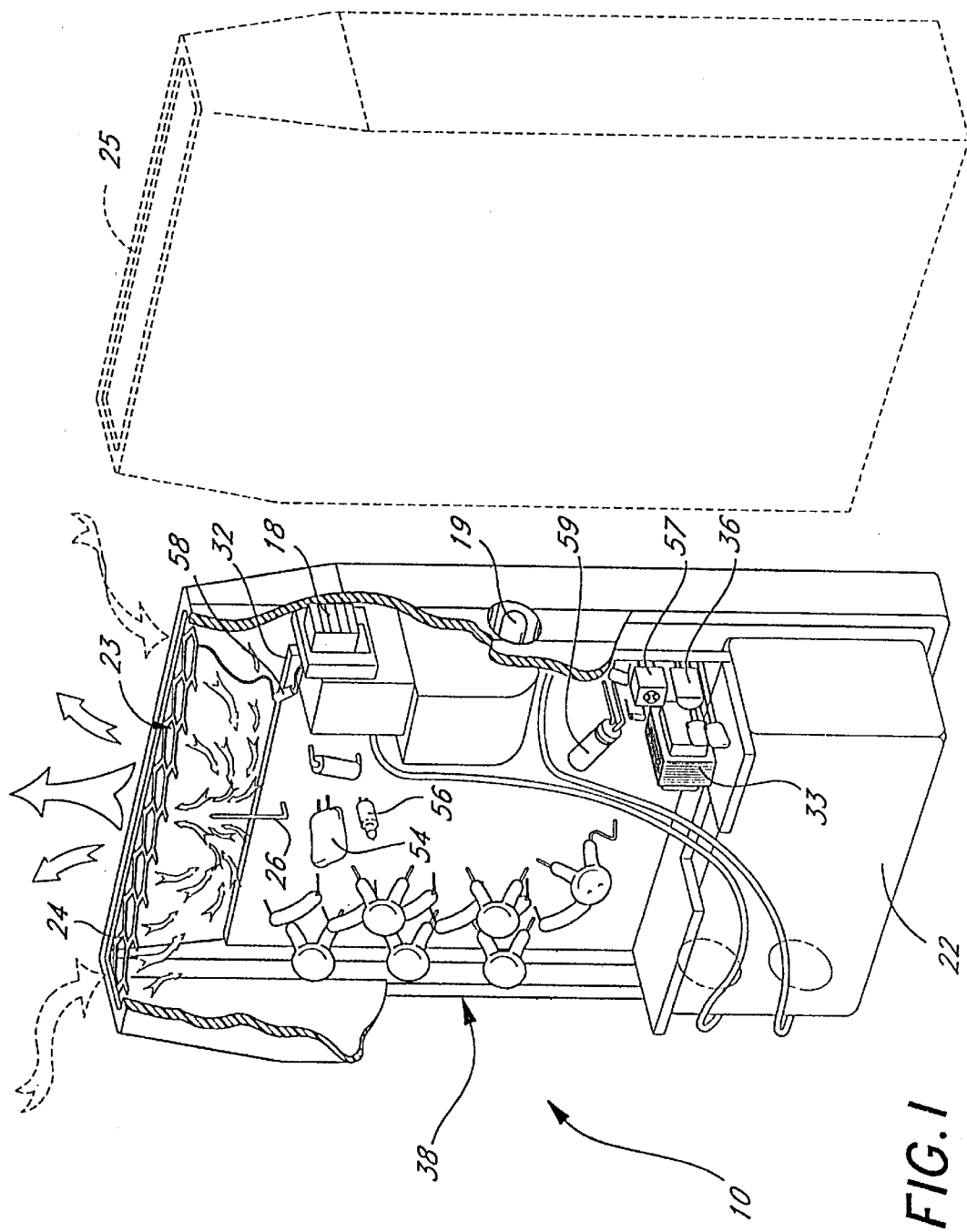
FIG. 1 shows a perspective drawing of the present invention.

FIG. 1 shows a perspective drawing of one embodiment of an air purifier 10 of the present invention cut away to show interior construction. It is shown next to an outline 25 of a conventional pager to indicate the unit size. This represents a considerably smaller package than that provided by this inventor's earlier invention or of any other portable air purifier of which this inventor is aware. The unit is generally rectangular with an ON/OFF switch 18 and a connector 19 for an AC battery adapter. The miniature electronics of the unit 10 are powered by a conventional nine-volt alkaline battery when the adapter is not connected.

The upper end of the unit 10 bears an opening 23 covered by a metallic grid 24 through which the purified air exits. A metallic needle-like emitter point 26 is mounted on a high voltage circuit module 32 and is located about ¼-inch below the grid 24. In use air near the emitter point 26 becomes ionized by a corona discharge developed by a high voltage (about 8 kV) supplied by the high voltage circuit module 32. It is important to note that while prior art devices, including the present inventor's earlier air purifier, generally use higher voltages, i.e., 15 kV or higher, it was unexpectedly discovered during the development of the present invention that lower voltages, i.e., below about 10 kV, yield a vigorous corona discharge and mass air flow while producing a dramatically lower level of ozone. Further, those of ordinary skill in the art will realize that either a positive or negative high voltage can be used to produce a corona discharge. The electronic circuits described below can be configured to produce either positive or negative high voltage. The unit operates adequately with either positive or negative corona discharge.

The metallic grid 24 is preferably nickel plated with about 80% open area and is held at ground potential relative to the emitter point 26 so that ions produced in the corona discharge are accelerated towards the grid 24. This results in a mass flow of air (i.e., the ionized molecules pull along a large number of nonionized molecules by means of cohesive forces) which propels the purified air out through openings (large arrows) in the grid 24. As purified air exits and is propelled towards the face of the wearer, room air (dotted arrows) is drawn in at the sides of the opening 23. At the same time the corona discharge provides ionizing energy and ozone to chemically destroy pollutants or pathogens through electron (plasma) impact decomposition. By adjusting the process to produce less ozone one is better able to balance ozone to average pollutant load. The majority of ozone is consumed reacting with pollutants before the air exits the purifier 10. Particulate matter produced during this destruction process is usually charged so that it is accelerated towards and precipitates on the metallic grid 24.

As a further improvement in reducing the emission of ozone, it is possible to coat the metallic grid 24 with a layer of Manganese Chloride, $M_N CL_2$, or Manganese Dioxide, $M_N O_2$, to act as a catalyst in converting the ozone into oxygen. It is believed that such a coating can further reduce the ozone level by 20% to 30%.

FIG. 2 shows a perspective drawing of an alternate embodiment of the air purifier 10'. This unit is the same size as the unit of FIG. 1 and uses the same improved electronics that will be explained below. The major difference between this unit 10' and the unit 10 of FIG. 1 is the ability of this alternate embodiment to utilize modern filtering materials to remove pollutants and pathogens prior to the corona discharge. The unit is of the same dimensions as the unit of FIG. 2 but also has an air intake 12 on one of its larger side surfaces. The air intake 12 is covered by a removable filter 14 held in place by a strip 16 of VELCRO® hook and loop fastener or some similar fastening system. Like the device of FIG. 1, unit 10' also has an ON/OFF switch 18 and a connector 19 for a battery adapter and is powered by a conventional nine-volt alkaline battery cell 22.

While the mass flow of air provided by the corona discharge is adequate to propel a stream of purified air out of the device, as explained in relation to FIG. 1, the inventor has found that the discharge mediated flow is generally not sufficient to pull air through a particulate or pollutant removing filter. Therefore, a miniature fan 15 has been provided. This fan is preferably one of the DC brushless types and operates at a low speed and uses very little power because its only task is to move air through the filter 14. Alternatively, a piezoelectric fan can be substituted for the brushless DC fan. FIG. 3 shows a simple diagram of the filter 14, fan 15, and emitter point 26 arrangement. Air is drawn through the filter 14 by the fan 15. The filtered air is then ionized by the emitter point 26 and is accelerated towards the grid 26. In nonportable prior art devices, fans have been used to move air through filters and propel it out of the device. Such powerful fans consume too much electricity for use in a portable device. The present inventor has found a low power alternative which uses the fan solely to pull air through the filter. The filtered air is then accelerated out of the device by the corona discharge.

The filter 14 can contain any of a number of filter materials. A HEPA (High Efficiency Particulate Air) filter can be used to remove both particulates and pathogens. Other popular filtering material such as glass wool or polyvinyl acetal sponge can be advantageously used to remove particulates and pathogens. Alternatively, a filter impregnated with a germicidal agent such as iodine can be used for pathogen inactivation. An activated carbon filter such as those of activated coconut charcoal can be included to remove chemical pollutants. Zeolite filtering materials can also be used to efficiently remove pollutants. All that is necessary is to ensure that the filter material is sufficiently porous that the fan 15 is able to pull sufficient air through the filter 15.

While the optional filter 14 directly absorbs particulates and toxic materials, the corona discharge actually destroys many pollutants not trapped by the filter 15. A corona discharge is an unusually powerful oxidizing source. Ozone produced by the discharge is chemically very active and oxidizes many pollutant chemicals and also inactivates pathogens and allergens. Besides ozone-mediated oxidation, there is tremendous destruction of airborne chemicals by direct electron (plasma) impact decomposition within the corona discharge. Particulates passing through the discharge without being incinerated become charged so they precipitate out on grounded surfaces like the metallic grid 24. Organic chemical decomposed by the corona discharge often yield particles of carbon that also precipitate out on the grid 24. In actual operation the discharge-facing surface of the grid 24 often becomes blackened and coated with precipitated and oxidized material. An advantage of using a filter to remove some of the organic pollutants prior to the corona discharge is that this prevents some of the precipitation on the grid 24 thereby extending the period of time between grid cleaning.

During the development of the present device the inventor discovered that it is important to adjust the rate of air movement through the corona discharge to obtain optimum destruction of pollutants. If the air moves too rapidly, the pollutants do not spend sufficient time in the discharge to ensure their destruction. The rate of air movement is affected by the potential difference and the geometrical relationship between the emitter point 26 and the grid 24. In the case of the embodiment with the fan 15, it is important to adjust the fan 15 and the filter 14 so that that the air is not propelled too rapidly through the corona discharge. With the present geometry and accelerating voltage the optimum rate of air flow out of the grid is about 50 ft/min. At lower flow rates the expelled air may not reach the user's face. At higher flow rates there is insufficient residence time in the corona discharge to obtain optimal destruction of pollutants.

Figure 4:
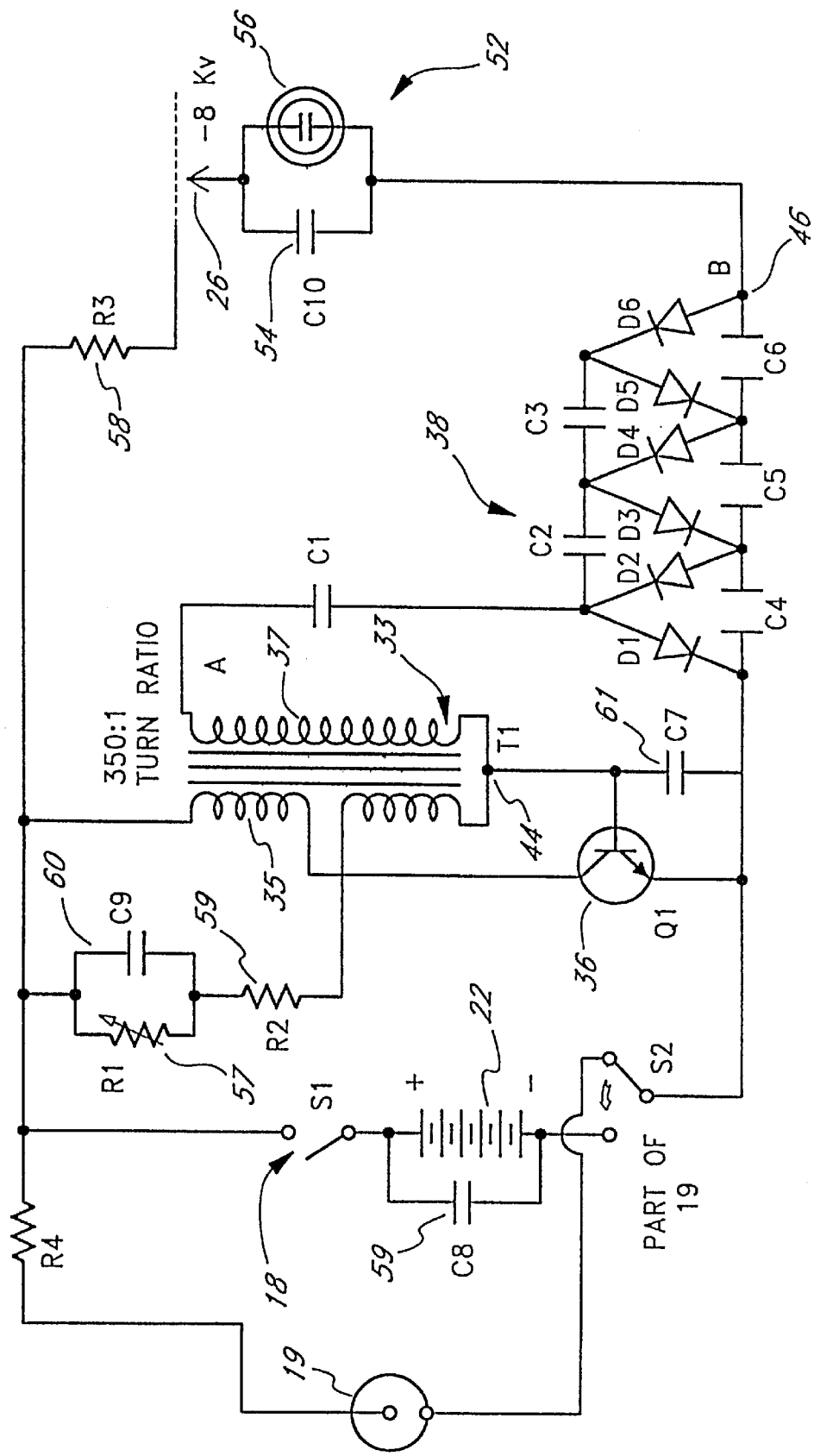
FIG. 4 shows a diagram of an electronic circuit of the present invention.
Figure 5:
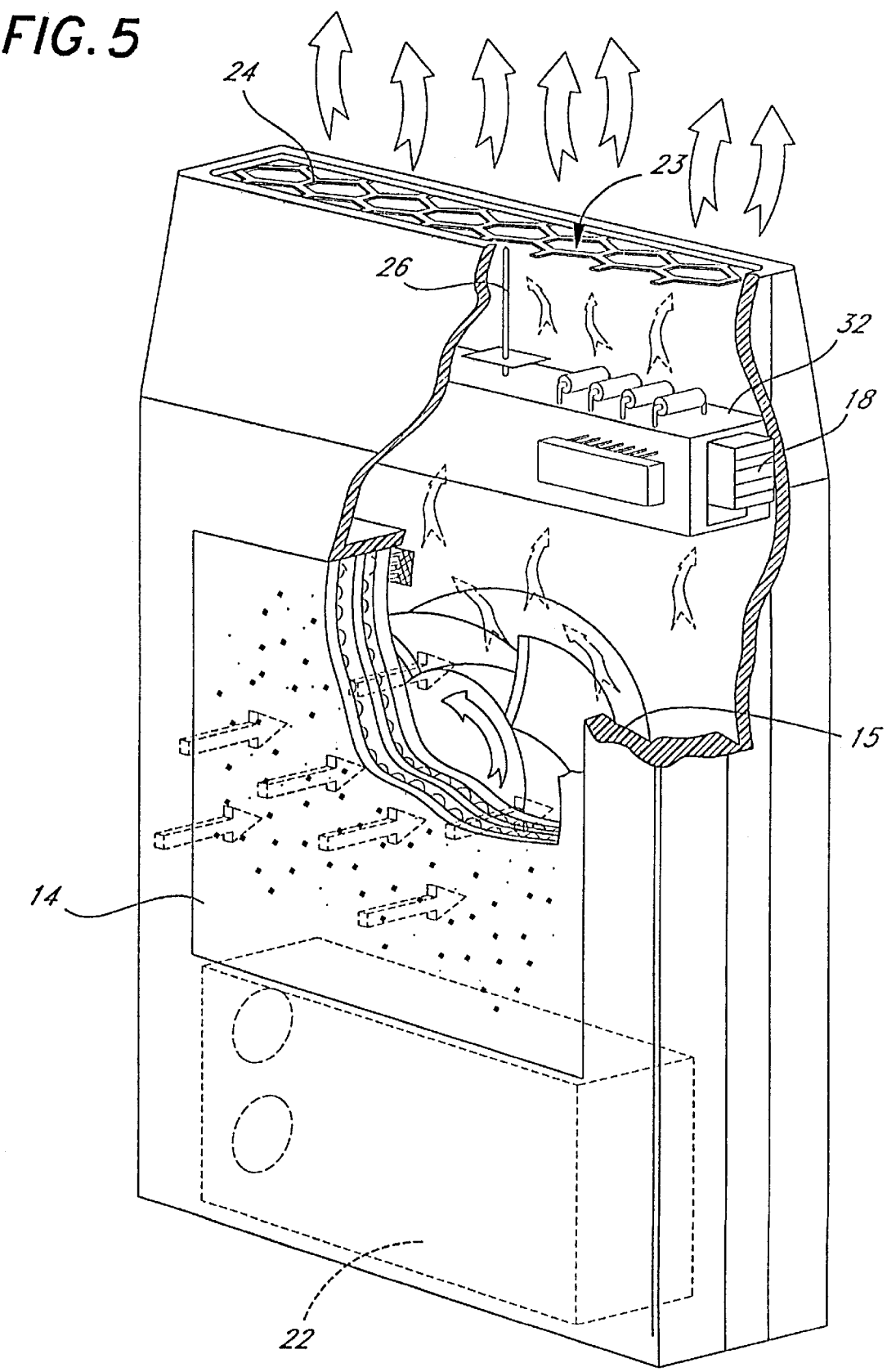
FIG. 5 shows a cut-away view of the embodiment of FIG. 2 showing the flow of air.

FIG. 4 shows a circuit diagram of the miniature electronics of the high voltage circuit board 32. This circuit allows the unit 10 to be very small and light while also providing unusually long battery life. While it is desirable to have ozone present in the corona discharge zone so as to help inactivate chemicals and microbes, the potential for ozone-caused irritation of mucous membranes makes it desirable to minimize the number of ozone molecules that actually reach the wearer of the unit. In experimenting with the prototypes of the present invention in an effort to balance air flow and battery life, the present inventor made a surprising discovery concerning ozone generation. When current flow into the high voltage generation system is limited and the high voltage kept below about 10 kV, and preferably at no more than about negative 8 kV, the level of emitted ozone drops dramatically without significantly impacting the mass air flow at the grid 24. This reduction of ozone production results in the electron impact effect of the corona discharge predominating.

The unit contains a ferrite transformer T1 33 having a primary coil 35 and a secondary coil 37 with a secondary/primary ratio of about 350/1. Current flow from the battery 22 (by way of S1 18) through the primary coil 35 is controlled by an NPN transistor Q1 36, such as low voltage Toshiba C 3279. The transistor 36 and transformer 33 form a step-up voltage inverter which converts battery DC into AC at a higher voltage. As current begins to flow from the battery 22, through the primary coil 35 and the transistor 36, it creates a rising magnetic field which induces a first rising voltage in the secondary coil 37. The winding ratio results in the voltage being multiplied to range between 0 and about 2,000 volts, while the primary voltage varies between 0 and 9 volts. The gate 42 of the transistor 36 is attached to a center tap 44 on the transformer 33. The rising voltage at the center tap 44 eventually causes the transistor 36 to switch off the current flow through the primary coil 35, causing the magnetic field in the secondary coil 37 to collapse.

Figure 6:
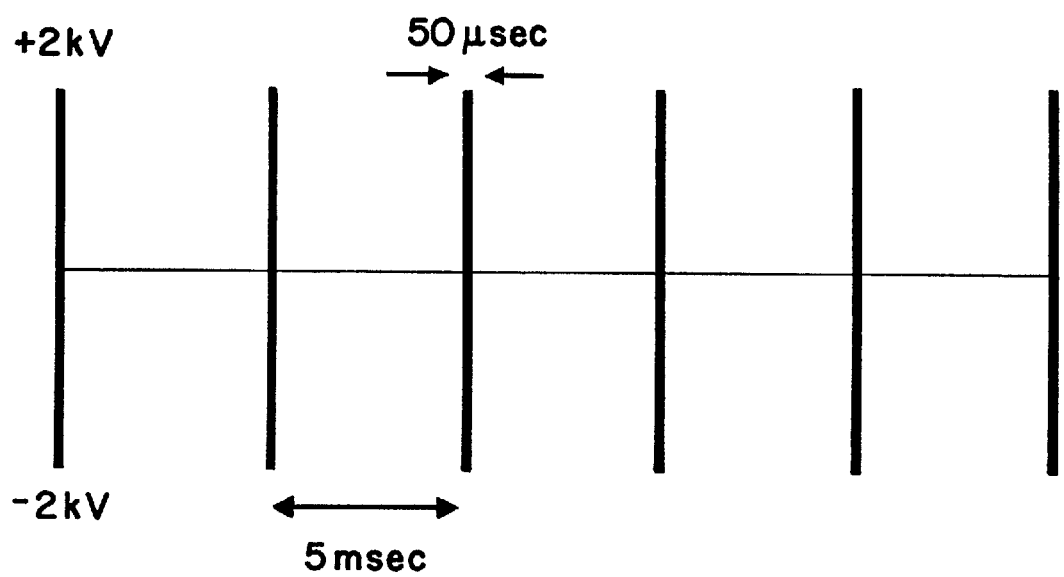
FIG. 6 is a graphic diagram of the voltage spikes produced by the circuit of FIG. 4.
Figure 7:
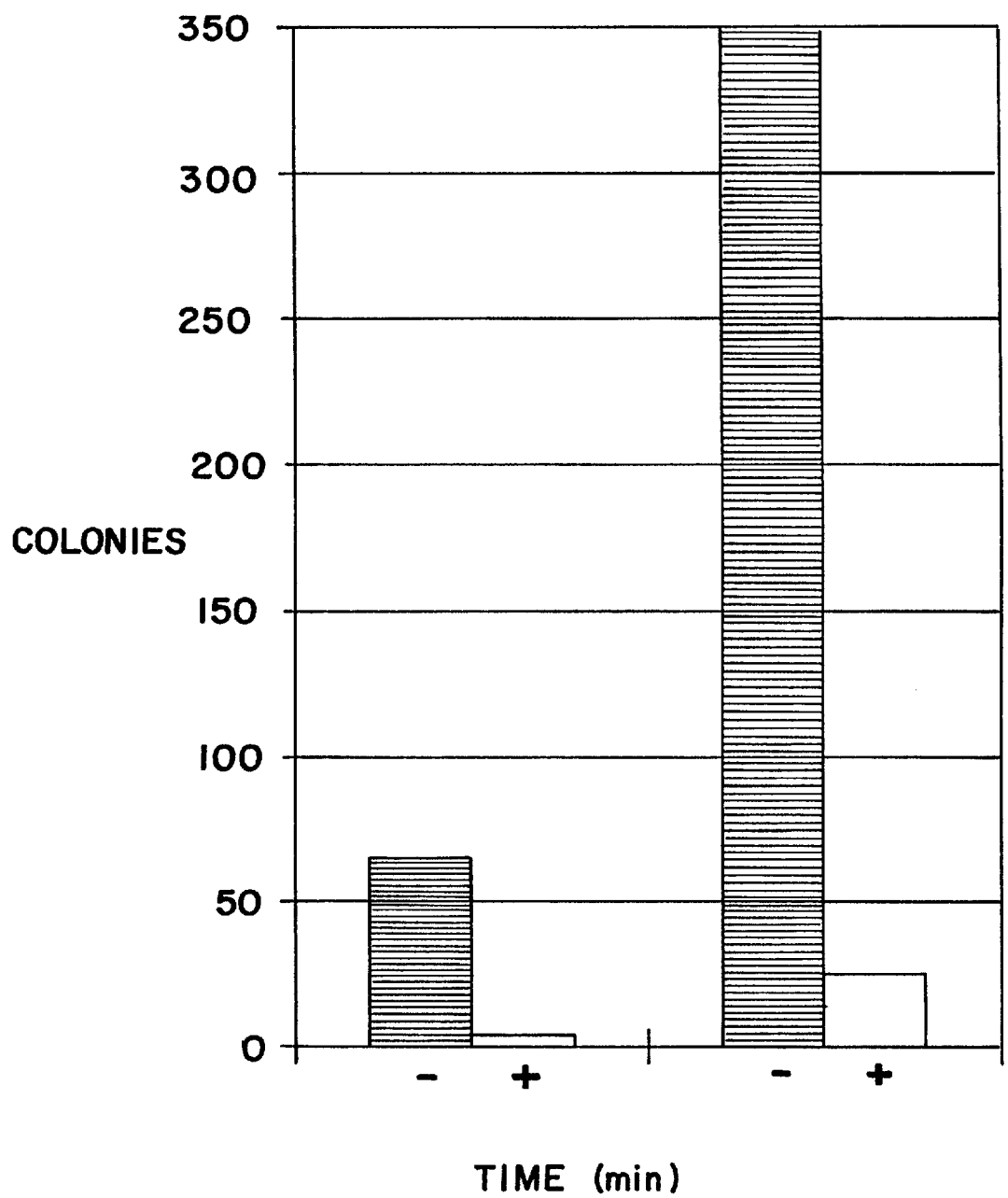
FIG. 7 is a graph showing the destruction of air borne bacteria by the present invention.
Figure 8:
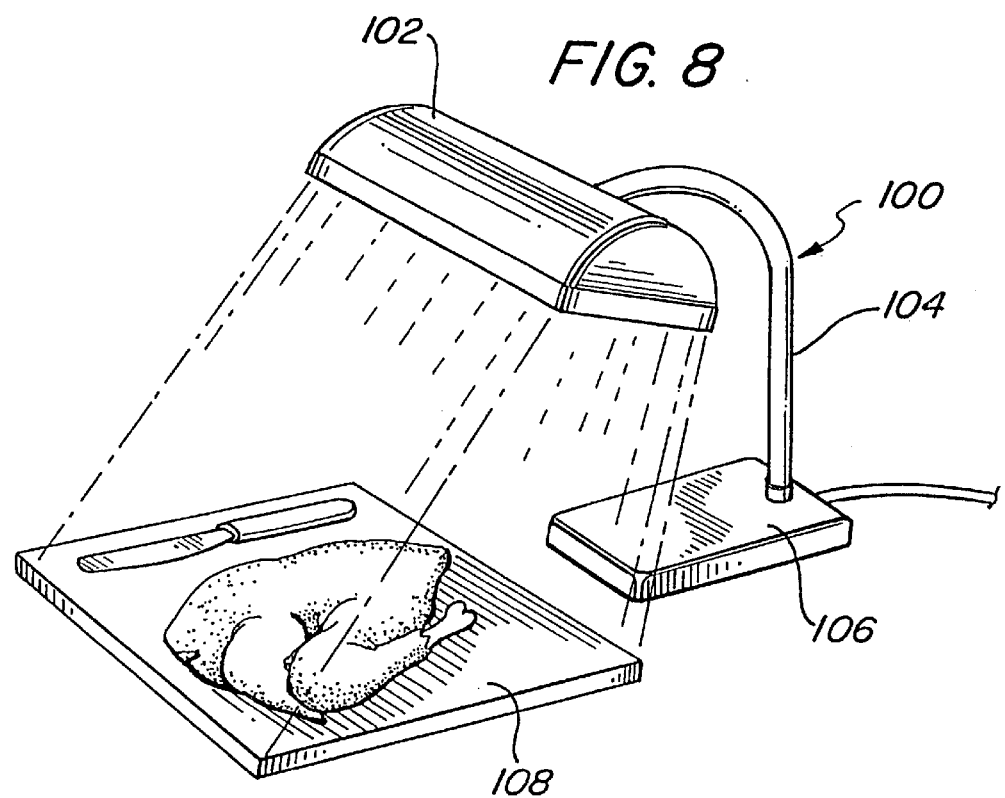
FIG. 8 is a prospective view of a modification of the air purifier for use with food products.
Figure 9:
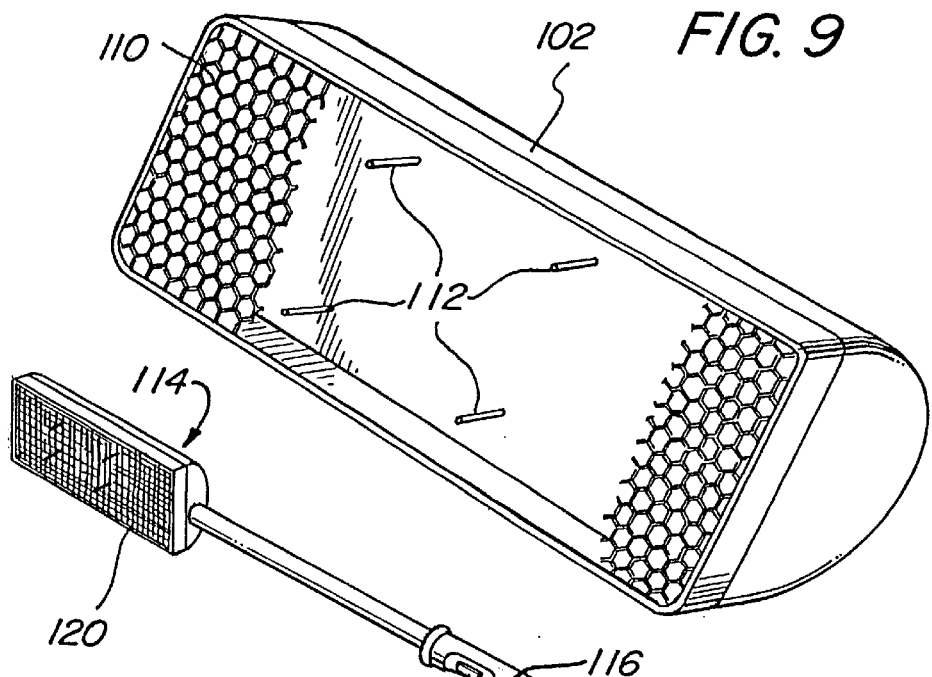
FIG. 9 is a partial prospective view of the hood of FIG. 8.
Figure 10:
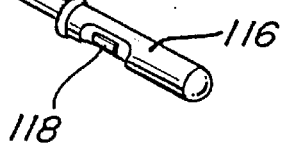
FIG. 10 is a prospective view of an alternative hand held wand-type of sterilizer.

The collapse of the magnetic field in the transformer T1 33 induces a second voltage, of the opposite polarity to the first voltage, in the secondary coil 37. The present inventor has found that using a resistance-capacitance network to shape the alternating current produced by the secondary coil 37 can dramatically alter the power consumption of the overall circuit. Resistors R1 (variable resistor to tune the circuit), and R2 and capacitors C8 59, and C9 60, and C7 58 adjust the circuit from one that would produce a sinusoidal voltage at Point A 34 to one that produces a series of high voltage spikes. The voltage at Point A 34 varies in polarity from about +2 kV to about −2 kV volts at a frequency of about 200 Hz. Because the output is voltage spikes, the circuit draws only about 10 mA so that a nine-volt battery lasts for about 60 hours. This frequency also appears to be important at getting minimal ozone production while maximizing the other effects of the corona discharge. FIG. 6 illustrates the high voltage spikes produced by the circuit. The output consists of pulses or spikes wherein each spike actually consists of a high voltage burst of about 50 microsecond duration every 5 msec. The tuning circuit mentioned above effectively performs pulse position modulation with a higher frequency of pulses consuming more current and resulting in a higher air flow. R1 57 can be adjusted for each unit so that the optimal pulse frequency of about 200 Hz can be set despite component variations from circuit board to circuit board.

The high voltage spikes are fed into a high voltage multiplier 38. The illustrated circuit is configured as a negative high voltage multiplier, but the circuit can also be configured as a positive high voltage multiplier. The presently preferred design of the multiplier 38 acts as a voltage sextupler with multiple stages and a final pulsating output voltage of about −8 kV at Point B 46. The high voltage multiplier 38 has stages containing high voltage (8 kV) diodes (D1–D6), and 6 kV, 100 pF ceramic capacitors (C2–C6). A specially selected hot melt adhesive is used to comnformationally coat the high voltage circuits to prevent inappropriate corona discharge and to encapsulate the system against moisture and other environmental factors. This treatment significantly reduces energy requirements further adding to overall increase of battery life. This encapsulation results in much lower finished device weight (an important factor for wearability) than conventional epoxy potting techniques.

The high voltage produced by the multiplier 38 is connected to the emitter point 26 by relaxation oscillator 52 which consists of a capacitor C10 54 (0.015 mF) and a 100-volt neon lamp 56 connected in parallel. As electrons flow through the emitter point 26, the neon lamp 56 flashes. This serves two purposes. First, it limits the current flow, and second, it serves as a visual cue that the unit is operating properly. Since the discharge is virtually without sound, the visual cue is especially helpful. The emitter point 26 is located about ¼–½-inch from the metallic grid 24, which completes the circuit to the battery through a 10 megOhm resistor R3 58, which further limits the current flow.

The disclosed grid-emitter geometry combined with the disclosed circuit produces a discharge current flow of about 5 $\mu$A at an air flow rate of 50 ft/min. At this current flow, according to Coulomb's law, there are about 31,000,000,000 electrons per second available in the corona discharge for ionizing and destroying pollutants through electron impact.

Besides the physical sensation of moving cold air there is an additional "psychological" effect of well-being experienced by the user inhaling the stream of purified air. Some of this effect is probably psychological due to the "clean, outdoor" smell and taste of the mildly ozonated air. It is widely believed that the refreshing quality of the outside atmosphere following the passing of a thunderstorm is due to this ozone effect. An additional cause of the "psychological" effect could well be an actual physiological response to trace levels of nitric oxide in the ionized air stream. Nitric oxide has recently been found to be an important biological signaling molecule that is involved in neural impulse transmission and a host of other biological phenomena. It is also known that application of nitric oxide to the lung reduces pulmonary blood pressure and acts as a broncodilator. Nitric oxide production seems to require a negative plasma source while most of the other effects discussed above can be obtained through either negative or positive corona discharge.

Nitric oxide my also contribute to the germicidal effect of the unit. Experiments performed by blowing bacteria laden air onto an exposed Petri plate surface have shown a dramatic drop in bacterial colonies when the contaminated air flow passes near to the grid 24 of a working air purifier 10 before striking the Petri plate. Presumably, germicidal agents emitted by the device destroy air borne bacteria. Also, some of the contaminated air is probably drawn into the actual corona discharge and directly disinfected. FIG. 7 graphically shows the results of blowing bacteria laden air onto exposed Petri plates for different periods of time. A first bar (−) in each pair represents the number of bacterial colonies (plates counted after incubation overnight at 37° C.) on plates after two or eight minutes of exposure to a steam of bacteria laden air. A second bar (+) in each pair represents the number of colonies when the bacterialaden air stream passed over an operating unit of the present invention before striking the Petri plate. Various control plates indicated that the bacteria were actually killed and not merely deflected by the stream of disinfecting air released by the present invention. The disinfecting air reduced the number of bacterial colonies by 90% (statistically significant at the 5% level). This dramatic effect was unexpected and opens the possibility of developing a bacteria shield. Such a device could be used in place of a surgical mask and would protect both the patient and the surgeon. Significantly, negative corona discharge was at least 20% more effective at destroying bacteria strongly suggesting that nitric oxide plays an important role in disinfection.

The present invention can also be used as a sterilizer for food preparation. As shown in FIG. 8, a sterilizer 100 can be mounted adjacent a kitchen counter or a cutting board 108 to aerosolize the surface and thereby reduce bacteria. The corona discharge provides an oxidizing environment that is believed to destroy bacterial spores and toxic organic material. Experiments on *E.coli* MV1190 and *E.coli* MC4100 indicated a 90% microbial neutralization. It is believed that equivalent results will be obtained with pathogenic strains of *E.coli*, such as *E.coli* 0157-H-7.

The sterilizer 100 includes a base or support member 106 with an adjustable column 194 that supports a hood member 102. In one form of the invention, shown in FIG. 9, the hood member 102 has four emitter points 112 mounted behind the grid 110. A series of circuit boards, such as shown in FIG. 1, can be used to drive each respective emitter point. The power supply can use a conventional A.C. 110 volt source with an AC/DC converter in the base member 106 to provide a 9 volt D.C. source for the circuit boards. Additionally, since the ozone would not be generated adjacent an inhalation area of the user, the voltage can be greater than about 8 kV.

An alternative embodiment of a hand held sterilizer 114 is shown in FIG. 10. The hood or housing portion 120 can be similar to the hood member 102 of the embodiment of FIG. 9. An extended handle 116 can support a 9 volt D.C. source, such as a 9 volt battery or six 1.5 volt AA batteries in series. An off/on push button trigger or switch 118 can activate a corona discharge and the user can pass the hood portion 120 directly over the surface or food to be sterilized. Preferably, the hood portion will be positioned very close, e.g., 1 inch to ¼ inch to the surface.

It is believed that the pathogens that can be acted upon by the sterilizer will not develop a resistance strain of pathogens as so often happens in drugs and other forms of bacteria controls.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A wearable personal corona discharge air purifier comprising:

- a low voltage electric power source;
- a metallic member electrically connected to a first terminal of the electric power source;
- a high voltage supply connectable to the electric power source for producing a corona discharge, the high voltage supply comprising:
  - a transformer; with a primary and secondary winding;
  - a transistor oscillator controlling current flow through the transformer so that the transformer outputs an alternating current with a peak to valley potential difference greater than a potential difference across the electric power source; and
  - a high voltage multiplier connected to the secondary winding to convert the alternating current into pulsating direct current, relative to the electric power source, at an output of the voltage multiplier; and
  - an emitter point connected to the output of the voltage multiplier and spaced apart from the metallic member, a corona discharge created around the emitter point ionizing air to form ions which ions are accelerated towards the metallic member by a potential difference between the metallic member and the emitter point.

2. The air purifier of claim 1, wherein the high voltage multiplier comprises a negative voltage multiplier producing a high negative voltage.

3. The air purifier of claim 1, wherein the high voltage multiplier comprises multiple stages, each stage comprising a high voltage diode and a capacitor.

4. The air purifier of claim 1, wherein the peak to valley potential difference of the alternating current output by the transformer is 200 to 400 times greater than the potential difference across the electric power source.

5. The air purifier of claim 1, wherein the alternating current output by the transformer is a series of voltage spikes rather than a sinusoidally varying voltage.

6. The air purifier of claim 5, wherein the series of voltage spikes has a frequency of about 200 Hz.

7. A wearable personal corona discharge air purifier comprising:

- a battery;
- a metallic member electrically connected to a positive terminal of the battery;
- a high voltage supply connectable between the terminals of the battery for producing a corona discharge, the high voltage supply comprising:
  - a transformer having a primary and a secondary coil;
  - a transistor with a tuning circuit controlling current flow through the primary coil of the transformer, said transistor having a gate connected to a tap of the transformer to form an oscillator feeding an alternating current into the primary coil of the transformer so that the secondary coil of the transformer outputs an alternating current of voltage spikes having voltage maxima of alternating polarities, said tuning circuit setting a frequency of the voltage spikes; and a high voltage multiplier connected to the secondary coil to convert the alternating voltage spikes into a pulsating direct current, at an output of the multiplier; and an emitter point connected to an output of the voltage multiplier, for creating a corona discharge around the emitter point, forming ozone, nitric oxide, and negative air ions, which ions are accelerated towards the metallic member by a potential difference between the grid and the emitter point causing a mass flow of air through the metallic member.

8. The air purifier of claim 7, wherein the high voltage multiplier comprises multiple stages, each stage of the multiplier comprising a high voltage diode and a capacitor.

9. The air purifier of claim 7, wherein the series of voltage spikes has a frequency of about 200 Hz.

10. A wearable personal corona discharge air purifier comprising:

an electric power source;

a metallic member electrically connected to the electric power source;

a high voltage supply connectable to the electric power source for producing a voltage, the high voltage supply comprising:

a step-up power inverter for providing an alternating current with a greater peak to valley potential difference than a potential difference across the electric power source; and a high voltage cascade multiplier connected to an output of the inverter to convert the alternating current into pulsating direct current, at an output of the cascade voltage multiplier; and a needle emitter point connected to the output of the voltage multiplier and spaced apart from the metallic member, for creating a corona discharge, ions formed by the corona discharge being accelerated towards the metallic member by a potential difference between the metallic member and the emitter point.

11. The air purifier of claim 10, wherein the high voltage cascade multiplier comprises multiple stages, each stage comprising a high voltage diode and a capacitor arranged as a cascade series voltage multiplier.

12. The air purifier of claim 10, wherein the alternating current produced by the voltage inverter is a series of high voltage spikes as opposed to a sinusoidally varying voltage.

13. The air purifier of claim 12, wherein the high voltage spikes output by the inverter each have a potential of about 2 kV.

14. The air purifier of claim 13, wherein the series of voltage spikes has a frequency of about 200 Hz.

15. The air purifier of claim 14, wherein each voltage spike comprises a voltage burst of about 50 $\mu$sec duration.

16. A sterilizing corona discharge air and surface purifier comprising:

an electric power source;

a metallic member operatively connected to the electric power source;

a high voltage supply connectable to the electric power source for producing a corona discharge, the high voltage supply comprising:

a transformer; with a primary and secondary winding;

a transistor oscillator controlling current flow through the transformer so that the transformer outputs an alternating current with a peak to valley potential difference greater than a potential difference across the electric power source; and a high voltage multiplier connected to the secondary winding to convert the alternating current into pulsating direct current, relative to the electric power source, at an output of the voltage multiplier; and at least one emitter point connected to the output of the voltage multiplier and spaced apart from the metallic member, a corona discharge created around the emitter point ionizing air to form ions which ions are accelerated towards the metallic member by a potential difference between the metallic member and the emitter point, whereby a gas discharge is directed from the metallic member to encourage a microbial neutralization of a surface.

17. The sterilizer of claim 16, wherein the high voltage multiplier comprises a negative voltage multiplier producing a high negative voltage and comprises multiple stages, each stage comprising a high voltage diode and a capacitor.

18. The sterilizer of claim 16, wherein a plurality of emitter points are provided adjacent the metallic member.

19. A hand held sterilizing corona discharge air and surface purifier comprising:

a housing;

a metallic member positioned on the housing;

at least one emitter point positioned adjacent the metallic member;

a power circuit connected to the emitter point for providing a corona discharge to ionize air to form ions, which ions are accelerated towards the metallic member by a potential difference between the metallic member and the emitter point, whereby a gas discharge is directed from the metallic member to encourage a microbial neutralization; and an outwardly extending handle connected to the housing to enable a user to sweep the housing across a surface to be sterilized, wherein the handle includes a D.C. battery source of power and an off/on switch for connecting the power circuit to the source of power.

20. A wearable personal corona discharge air purifier comprising:

a housing:

an opening in the housing for emitting purified air;

a member electrically connected to a terminal of a power source, said member positioned proximate the opening:

a high voltage supply in the housing and connected between the terminals of the power source for producing a corona discharge, the high voltage supply comprising:

a transformer having a primary and a secondary coil;

a transistor with a tuning circuit controlling current flow through the primary coil of the transformer, said transistor having a gate connected to a tap of the transformer to form an oscillator feeding an alternating current into the primary coil of the transformer so that the secondary coil of the transformer outputs an alternating current of voltage spikes having voltage maxima of alternating polarities; and a high voltage multiplier connected to the secondary coil to convert the alternating voltage spikes into a pulsating direct current, at an output of the multiplier; and an emitter point adjacent the opening and connected to an output of the voltage multiplier thereby creating a corona discharge of ions around the emitter point, which ions are accelerated towards the member by a potential difference between the member and the emitter, causing a mass flow of air from the housing.

21. The air purifier of claim 20 wherein a distance between the emitter point and the member is ¼ to ½ inches.

22. The air purifier of claim 20 wherein the member is a metallic grid.

23. The air purifier of claim 22 wherein said metallic grid is nickel plated.

24. The air purifier of claim 22 wherein said metallic grid is coated with a catalyst for converting ozone into oxygen.

* * * * *